United States Patent [19]

Thakkar et al.

[11] Patent Number: 4,775,659

[45] Date of Patent: Oct. 4, 1988

[54] INJECTABLE SEMI-SOLID FORMULATIONS

[75] Inventors: Arvind L. Thakkar, Indianapolis; Roger G. Harrison, Zionsville, both of Ind.

[73] Assignee: Eli Lilly and Company, Indianapolis, Ind.

[21] Appl. No.: 766,725

[22] Filed: Aug. 19, 1985

[51] Int. Cl.$^4$ ..................... A61K 37/36; A61K 37/18
[52] U.S. Cl. .......................... 514/12; 514/2; 514/21; 514/768; 514/964; 424/108; 424/499; 424/502
[58] Field of Search ............... 514/2, 12, 21, 768, 514/964; 424/108, 499, 502

[56] References Cited

U.S. PATENT DOCUMENTS

| | | | |
|---|---|---|---|
| 2,493,202 | 1/1950 | Macek | 167/82 |
| 3,869,549 | 3/1975 | Geller | 514/12 |

FOREIGN PATENT DOCUMENTS

| | | | |
|---|---|---|---|
| 0140255 | 5/1985 | European Pat. Off. | |
| 1081551 | 8/1967 | United Kingdom | 514/786 |

OTHER PUBLICATIONS

Takano et al., cited in Chem. Abstracts, vol. 99:64639.
Gelucire Product Bulletin published by Gattefosse Corporation (1983).
Davis et al., *J. Dairy Sci.*, 66:1980–1982 (1983).
Buckwalter et al., *J. of the American Pharmaceutical Assoc.* 47, 661–666 (1958).
Chemical Abstracts 52:20922b.
Chemical Abtracts 42:7934d.
Chemical Abstracts 31:5941–5944.
Chemical Abstracts 46:9809g.
Slevin et al., *Investigational New Drugs* 2, 271–276 (1984).
Chemical Abstracts 52:6731b.
Chemical Abstracts 51:13323f.
Chemical Abstracts 52:15845e.
Chemical Abstracts 51:9100d.
Chemical Abstracts 44:1225i.
Chemical Abstracts 39:4390–4394.
Chemical Abstracts 54:16756g.

*Primary Examiner*—J. R. Brown
*Assistant Examiner*—Jacqueline M. Stone
*Attorney, Agent, or Firm*—Bruce J. Barclay; Leroy Whitaker

[57] ABSTRACT

This invention provides injectable semi-solid formulations comprising a pharmaceutically or veterinary active agent, an oil and a suitable glyceride release modifying agent.

5 Claims, 2 Drawing Sheets

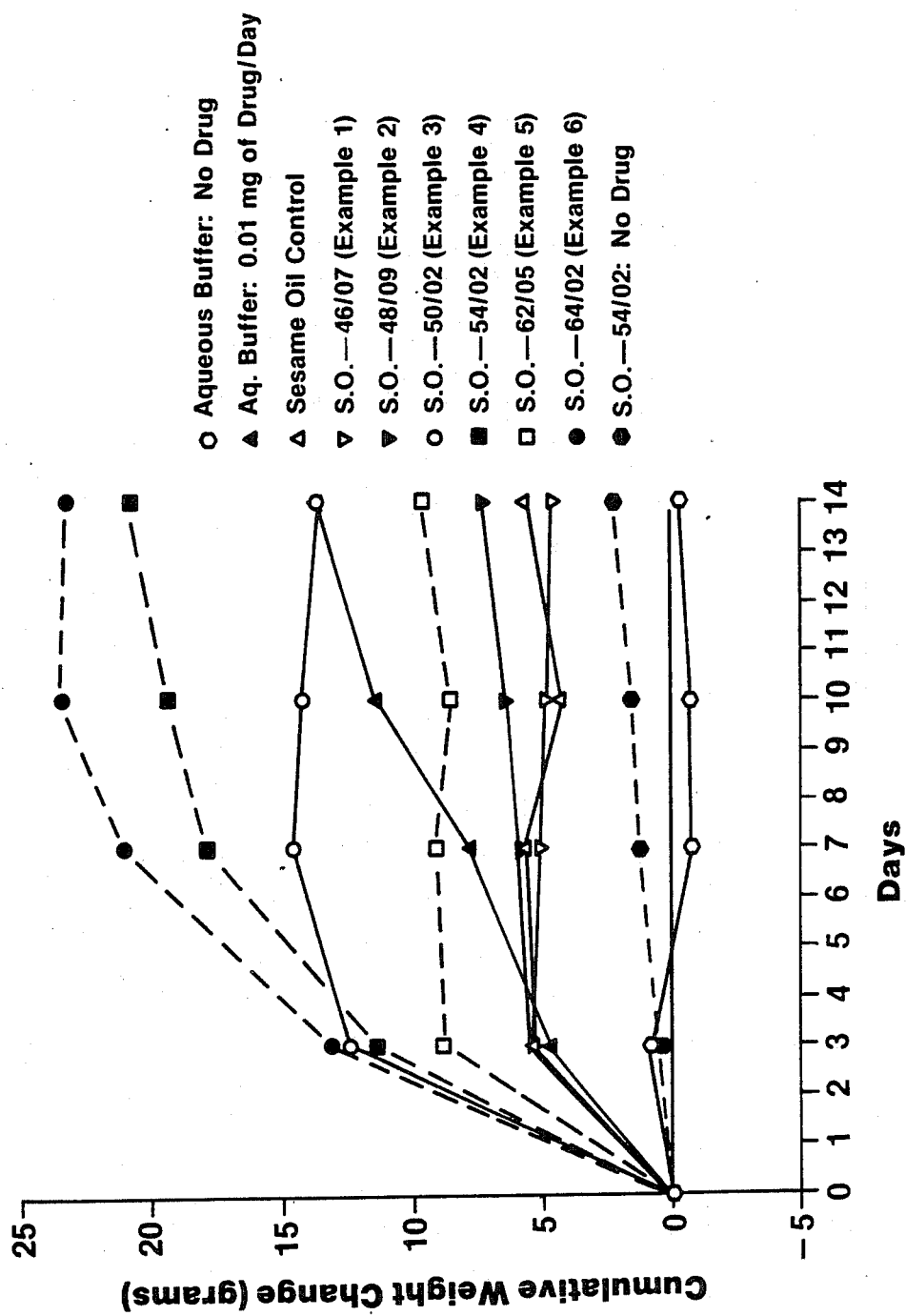

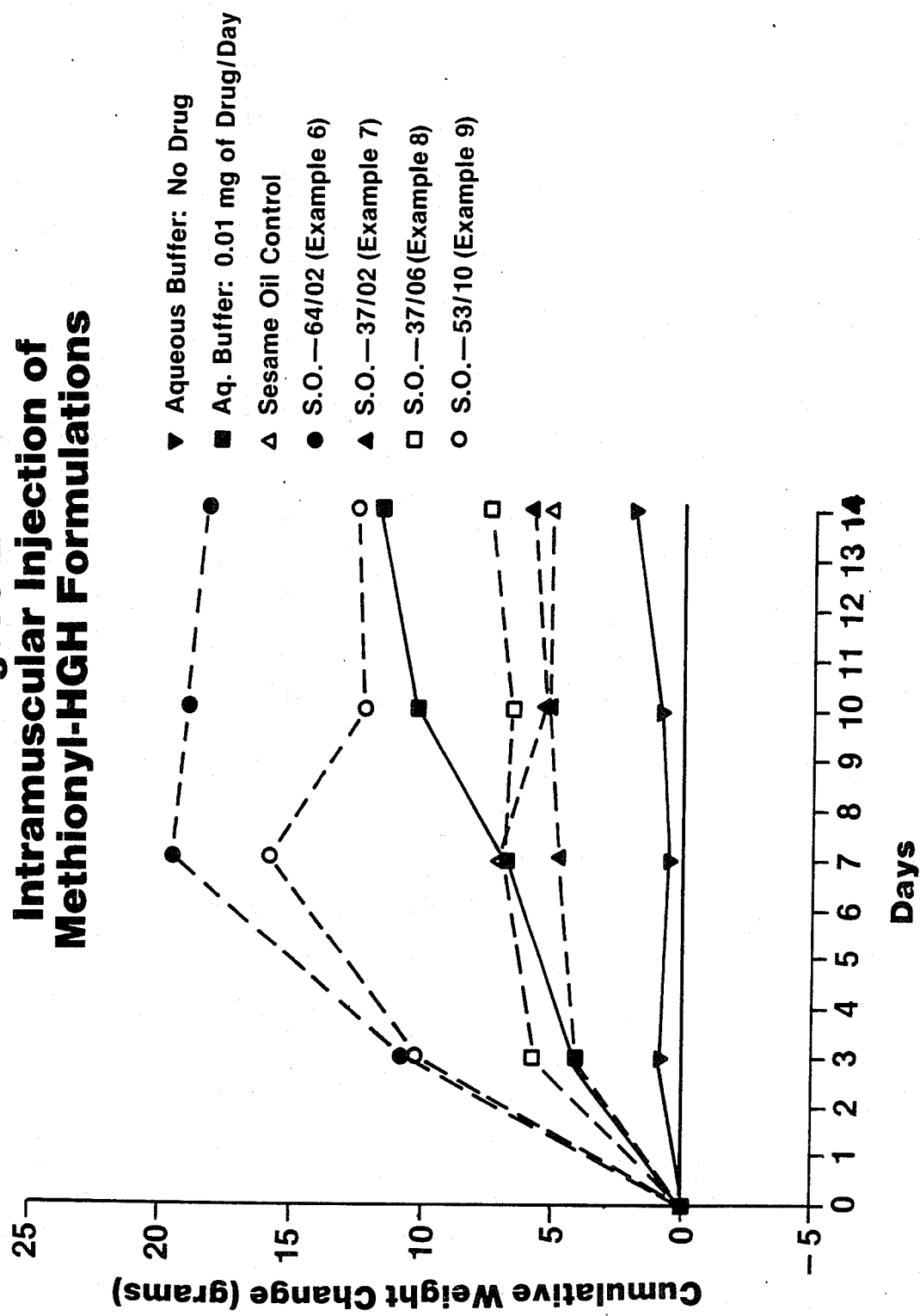

INJECTABLE SEMI-SOLID FORMULATIONS

SUMMARY OF THE INVENTION

The present invention provides a novel injectable pharmaceutical or veterinary formulation comprising from about 0.01% to about 5.0% by weight of a pharmaceutically or veterinary active agent, from about 60.0% to about 94.99% by weight of an oil and from about 5.0% to about 35.0% by weight of a suitable glyceride release modifying agent.

BRIEF DESCRIPTION OF THE DRAWINGS

FIGS. 1 and 2 illustrate the cumulative weight gain changes of certain formulations of the invention containing methionyl-HGH as compared to various control formulations. The formulations of the invention for which data is provided in the Figures are described in detail in the Examples. In the Figures, S.O. means sesame oil and the numerical values represent the type of Gelucire glyceride derivative tested. For example, 37/02 in FIG. 2 represents Gelucire 37/02.

DETAILED DESCRIPTION OF THE INVENTION

The quantities of ingredients employed in a formulation of the invention are set forth as percentages of the total weight of the formulation. It will be readily understood that the concentration ranges set forth herein for the ingredients of the formulations are approximations, and that minor variations to these ranges are believed to provide useful formulations contemplated within the scope of the present invention.

The formulations of the present invention are semi-solid injectable matrices containing an active agent, an oil and a suitable glyceride release modifying agent. These nonaqueous formulations provide sustained release of the desired active agent by formation of a viscous, semi-solid depot at the site of intramuscular injection. Once injected, these hydrophobic formulations are believed to slowly erode upon contact with aqueous biological fluid. By varying the hydrophobicity of a formulation of the invention, the release rate of the particular active agent may be varied as well. In the formulations of the invention, hydrophobicity is varied with a suitable glyceride release modifying agent.

The term "suitable glyceride release modifying agent" means a compound, or mixture of compounds, having a combined lipophilic and hydrophobic effect which is miscible in oil and which contains an ester of glycerol and one or more fatty acids. The glyceride release modifying agent employed herein will be a nonwaxy substance will have a melting point greater than that of the body temperature of the animal to which a formulation of the invention is administered, or approximately 37° C. Preferably, the glyceride release modifying agent will have a melting point in the range of about 50° C. to about 75° C.

The release modifying agents employed herein are amphiphiles in which the molecule or ion contains both hydrophilic and lipophilic portions. These agents can be defined by a numerical value based on the Hydrophile-Lipophile Balance system, called the HLB system. The HLB scale is a numerical scale, extending from 0 to approximately 50, where lower numbers denote more lipophilic and hydrophobic substances, and higher numbers denote more hydrophilic and lipophobic substances. The affinity of a compound for water, or for oily substances, is determined and its HLB value is assigned experimentally. Tables of such values have been published and formulation chemists are aware of them. The total HLB value of the present composition may be calculated from the individual HLB's of its various components. The HLB of the present composition will be in the range of about 1 to about 10, more particularly from about 1 to 5.

The preferred glyceride release modifying agents for use herein are sold under the trademark Gelucire by Gattefosse Corporation, Hawthorne, N.Y. Gelucires are available with a variety of HLB values and melting points. The preferred glyceride derivative from this series is Gelucire 64/02, meaning that the substance has a melting point in the range around 64° C. and an HLB value of about 2. Other preferred substances from this class include Gelucire 54/02 and Gelucire 50/02. A detailed discussion of the properties of Gelucire products is presented by C. Doelker et al. in "Incorporation of Liquid, Deliquescent, and Unstable Active Ingredients Into Excipients for Hard Gelatin Capsules", *Proceedings of the 3rd International Conference on Pharmaceutical Technology* (Paris), 73–82 (1983). The glyceride release modifying agent employed in a formulation of the invention will be present at a concentration in the range of about 5.0% to about 35.0% by weight of the total formulation, more preferably from about 10.0% to about 25.0% by weight of the total formulation.

An oil will be present in the composition of the present invention to act as a vehicle for injection. Suitable oils for parenteral administration of biologically active substances are well known to formulation chemists. These oils will preferably be of vegetable origin so that they may be readily biodegraded. The oil will ideally provide little or no muscular irritation upon injection. Further, these oils should be liquid at room temperature, and should be of the type that do not become rancid rapidly when stored. The oils will typically be esters of unsaturated fatty acids. Exemplary oil vehicles for use in the present compositions include corn oil, cottonseed oil, peanut oil, sesame oil, ethyl oleate, and the like, including other oil vehicles which would not interfere with the therapeutic efficacy of the biologically active ingredient included as part of the composition of the invention. The quantity of oil vehicle employed herein will be in a range of about 60.0% by weight to about 94.99% by weight of the total formulation, more preferably from about 75.0% to about 90.0% by weight.

A variety of pharmaceutically or veterinary active agents may be employed in the formulations of the invention. These active agents are of the type which can be used as injectables, and which will be comprised of one or more amino acid fragments, such as peptides or proteins, whether derived synthetically, biosynthetically or by recombinant DNA technology. Examples of these active agents include human growth hormone (HGH), and especially methionyl-HGH; insulin; insulin like growth factors 1 and 2; bovine growth hormone (BGH); growth hormone releasing factor; glucagon; proinsulin; interleukin 1, 2 and 3; colony stimulating factor; tissue activator of plasminogen; thrombomodulin; lipomodulin; skeletal growth factor; erythropoetin; interferons; factor VIIIc; atrial natriuretic factor; and related proteins and polypeptides. The active agent will be present in the formulation in a range of about 0.01% by weight to about 5.0% by weight of the formulation, or as otherwise required to provide the desired rate of release of active agent to the animal subject.

The present composition may also contain one or more antioxidants in order to provide stability to the formulation and to prevent the oxidation of the active agent and of the other components employed therein. These antioxidants will be of the type known for use in oil based pharmaceutical or veterinary compositions. Suitable antioxidants for use herein include α-tocopherol, ascorbyl palmitate, BHT and other like substances suitable for use in nonaqueous, oil based formulations. The quantity of antioxidant employed will be dictated by the amount of other ingredients present in the formulation, and the particular antioxidant, but will typically be in the range of about 0.01% by weight to about 10.0% by weight of the total formulation.

One or more preservatives may also be present in the composition of the invention to protect against the growth of potentially harmful microorganisms. Typical preservatives suitable for use herein include hexyl resorcinol and phenyl mercuric benzoate. These preservatives must be present at an adequate concentration in the composition so as to prevent the multiplication of microorganisms inadvertently introduced into the composition while withdrawing the composition from its container with a hypodermic needle and syringe. Generally, the preservatives will be present at a concentration in the range of about 0.05% by weight to about 1.0% by weight of the total formulation.

As noted above, the composition of the invention, once injected into an animal, will form a depot at the site of injection and slowly release the active agent over time. Compositions of the invention having an HLB in the desired range defined above are believed to function by partitioning of the active agent from the depot into the surrounding biological fluid. However, the present formulations are not limited by any mode of operation and this explanation is merely provided as a possible mechanism of action.

The formulations of the invention may be prepared by procedures generally known to formulation chemists. Typically, a matrix, consisting of an oil and a suitable glyceride release modifying agent, is prepared by adding the glyceride release modifying agent to the hot oil, that is, at a temperature in the range of about 50° C. to about 150° C., and stirring until a clear solution is obtained. The homogeneous mixture is then rapidly cooled with stirring. If necessary, any preservatives and antioxidants are next added. Finally, the active agent is blended into the matrix at a temperature that would not adversely effect its stability. The resulting mixture is then suitable for administration to the mammal in need of treatment with a composition of the invention.

The following Examples illustrate specific formulations of the present invention, and methods for their preparation. The Examples are not intended to be limiting to the scope of the invention in any respect and should not be so construed.

EXAMPLE 1

A glass vial was charged with 4.91520 g of a matrix containing 4.17792 g of sesame oil and 0.73728 g of Gelucire 46/07. A small stirring bar was added to vial and the contents of the vial were stirred at a temperature of about 65° C. until homogeneous. The vial was placed in a cold water bath and the mixture was stirred for about 20 minutes. The stirring bar was removed from the matrix and 0.05209 g of biosynthetically derived methionyl-HGH was added to provide a concentration of methionyl-HGH in the formulation of about 0.998 mg per 0.1 ml of formulation. The resulting formulation of the invention was stored in a refrigerator until needed for further study.

Following the general procedure of Example 1, additional formulations of the invention were prepared. These formulations are set forth below.

EXAMPLE 2

A glass vial was charged with 4.92723 g of a matrix containing 4.18815 g of sesame oil and 0.73908 g of Gelucire 48/09, and 0.05389 g of methionyl-HGH, and formulated as described in Example 1 to provide methionyl-HGH at a concentration of about 1.004 mg for each 0.1 ml of formulation.

EXAMPLE 3

Following the general procedure of Example 1, 4.92582 g of a matrix containing 4.18695 g of sesame oil and 0.73887 g of Gelucire 50/02 and was combined with 0.0557 g of methionyl-HGH to provide a formulation of the invention having a concentration of methionyl-HGH of 1.004 mg for each 0.1 ml of formulation.

EXAMPLE 4

Following the general procedure of Example 1, 4.65124 g of a matrix containing 3.95355 g of sesame oil and 0.69769 g of Gelucire 54/02 was combined with 0.05018 g of methionyl-HGH to provide a formulation of the invention having a concentration of methionyl-HGH of 0.990 mg for each 0.1 ml of formulation.

EXAMPLE 5

Following the general procedure of Example 1, 4.91816 g of matrix containing 4.18044 g of sesame oil and 0.73772 g of Gelucire 62/05 was combined with 0.05359 g of methionyl-HGH to provide a formulation of the invention having a concentration of methionyl-HGH of 1.000 mg for each 0.1 ml of formulation.

EXAMPLE 6

Following the general procedure of Example 1, 4.89041 g of matrix containing 4.15685 g of sesame oil and 0.73356 g of Gelucire 64/02 was combined with 0.05272 g of methionyl-HGH to provide a formulation of the invention having a concentration of methionyl-HGH of 1.004 mg for each 0.1 ml of formulation.

EXAMPLE 7

Following the procedure of Example 1, 5.069 g of matrix containing 4.30865 g of sesame oil and 0.76035 g of Gelucire 37/02 was combined with 0.05589 g of methionyl to provide a formulation of the invention having a concentration of methionyl-HGH of 1.002 mg for each 0.1 ml of formation

EXAMPLE 8

Following the procedure of Example 1, 5.052 g of a matrix containing 4.2942 g of sesame oil and 0.7578 g of Gelucire 37/06 was combined with 0.05585 g of methionyl-HGH to provide a formulation of the invention having a concentration of methionyl-HGH of 1.004 mg for each 0.1 ml of formulation.

EXAMPLE 9

Following the procedure of Example 1, 5.078 g of matrix containing 4.3163 g of sesame oil and 0.7617 g of Gelucire 53/10 was combined with 0.05707 g of methionyl-HGH provide a formulation of the invention having a concentration of methionyl-HGH of 1.006 mg for each 0.1 ml of formulation.

A sesame oil formulation was prepared by combining 5.00842 g of sesame oil and 0.05414 g of methionyl-HGH to provide concentration of 0.992 mg of methionyl-HGH per 0.1 ml of formulation.

The following procedure was employed to determine the sustained activity of compositions of the invention.

Seven female Sprague Dawley hypophipectmized 44 day old rats were administered by a single intramuscular injection with 0.1 ml of a specified formulation. Individual body weights were recorded just prior to administration and at 3, 7, 10 and 14 days after administration.

The data obtained by the above described experiment indicates the body weight increase observed with various formulations of the invention containing methionyl-HGH and is set forth below in Table I. In the Table, column 1 provides the Example Number of the formulation tested; column 2, the days after administration; column 3, the body weight increase in grams from the weight of the rat on day 0; and column 4, the standard deviation (SD) for the body weight change based on seven trials.

TABLE I

Body Weight Increase Observed with Formulations Containing Methionyl-HGH

| Example No. of Formulation | Days After Administration | Body Weight Increase (g) | SD |
|---|---|---|---|
| 1 | 3 | 5 | 3.0 |
|   | 7 | 5 | 2.6 |
|   | 10 | 5 | 3.6 |
|   | 14 | 5 | 3.0 |
| 2 | 3 | 5 | 1.5 |
|   | 7 | 6 | 1.1 |
|   | 10 | 7 | 1.3 |
|   | 14 | 7 | 1.5 |
| 3 | 3 | 12 | 1.0 |
|   | 7 | 15 | 2.8 |
|   | 10 | 14 | 2.6 |
|   | 14 | 13 | 2.9 |
| 4 | 3 | 11 | 4.6 |
|   | 7 | 18 | 2.5 |
|   | 10 | 19 | 4.4 |
|   | 14 | 21 | 4.0 |
| 5 | 3 | 9 | 2.8 |
|   | 7 | 9 | 5.1 |
|   | 10 | 9 | 5.3 |
|   | 14 | 10 | 5.5 |
| 6 | 3 | 13 | 1.7 |
|   | 7 | 21 | 1.6 |
|   | 10 | 23 | 3.4 |
|   | 14 | 23 | 3.1 |
| 7 | 3 | 4 | 1.8 |
|   | 7 | 5 | 2.1 |
|   | 10 | 5 | 2.2 |
|   | 14 | 6 | 2.1 |
| 8 | 3 | 6 | 1.2 |
|   | 7 | 7 | 1.1 |
|   | 10 | 7 | 1.1 |
|   | 14 | 8 | 2.5 |
| 9 | 3 | 10 | 1.8 |
|   | 7 | 15 | 2.7 |
|   | 10 | 12 | 2.4 |
|   | 14 | 12 | 3.4 |
| Sesame Oil Control | 3 | 5 | 0.8 |
|   | 7 | 6 | 1.1 |
|   | 10 | 4 | 1.7 |
|   | 14 | 6 | 2.4 |

FIGS. 1 and 2 illustrate the cumulative weight change of various formulations of methionyl-HGH following intramuscular injection. The data in these Figures is that which is presented in Table I as hereinbefore described. As can be noted from the Figures, in general, those formulations of the invention which contain Gelucire glyceride derivatives having higher melting points and lower HLB values gave preferred cumulative weight gain increases.

We claim:

1. An injectable pharmaceutical or veterinary formulation substantially free of fatty acid salts of aluminum comprising from about 0.01% to about 5.0% by weight of a pharmaceutically or verterinary active agent comprised of one or more amino acid fragments, from about 60.0% to about 94.99% by weight of an oil and from about 5.0% to about 35.0% by weight of a suitable glyceride release modifying agent.

2. A formulation of claim 1 wherein the pharmaceutically or veterinary active agent is methionyl-human growth hormone.

3. A formulation of claim 2 which has an HLB value in the range of about 1 to about 5.

4. A formulation of claim 3 wherein the glyceride release modifying agent has a melting point in the range of about 50° C. to about 75° C.

5. A formulation of claim 1 wherein the suitable glyceride release modifying agent is present at a concentration in the range of about 10.0% to about 25.0% by weight.

* * * * *